United States Patent [19]

Horn

[11] 4,046,139
[45] Sept. 6, 1977

[54] MEDICAL TEMPERATURE MEASURING DEVICE

[76] Inventor: Bernard Horn, 7742 Terrace Drive, El Cerrito, Calif. 94530

[21] Appl. No.: 716,657

[22] Filed: Aug. 23, 1976

[51] Int. Cl.² .......................... A61B 5/00; A61M 25/00
[52] U.S. Cl. .................................... 128/2 H; 128/351
[58] Field of Search ............... 128/2 R, 2 H, 2 S, 348, 128/349 B, 351

[56] References Cited

U.S. PATENT DOCUMENTS

| 3,081,765 | 3/1963 | Kompelien | 128/2 H |
| 3,373,735 | 3/1968 | Gallagher | 128/2 W |
| 3,499,435 | 3/1970 | Rockwell et al. | 128/2.05 R |
| 3,951,136 | 4/1976 | Wall | 128/2 H |

FOREIGN PATENT DOCUMENTS

| 790,091 | 9/1935 | France | 128/2 S |

OTHER PUBLICATIONS

Ellenwood et al., IBM Tech. Disclosure Bull., vol. 11, No. 11, Apr. 1969, 1565.

*Primary Examiner*—Dalton L. Truluck
*Attorney, Agent, or Firm*—Robert R. Tipton

[57] ABSTRACT

A medical temperature measuring device uses a pliant flexible tube adapted to enter the trachea and permit normal respiratory function with its interior end adapted to enter the trachea. On the interior end is disposed a temperature sensor for continuous monitoring of tracheal temperature. An inflatable cuff is provided proximate the interior end on which the temperature sensor is mounted to insure thermal contact with the tracheal wall. The temperature can also be mounted on the wall of the tube for thermal contact with the trachea. A thermal insulation can also provided between the air channel and the temperature measuring device to prevent temperature readings from being affected by cooler incoming air. The temperature sensor can also be a temperature indicating material that changes color at predetermined temperatures.

2 Claims, 8 Drawing Figures

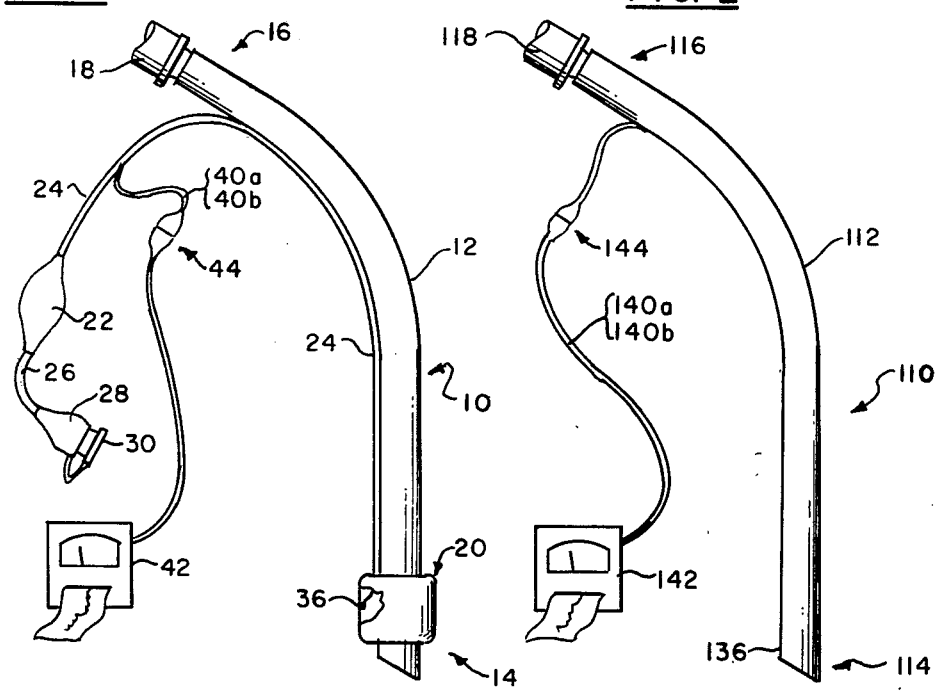

MEDICAL TEMPERATURE MEASURING DEVICE

BACKGROUND OF THE INVENTION

This invention relates generally to devices for measuring body temperature and in particular to devices and apparatus for measuring tracheal temperatures during operations.

During operations in which a patient is under anesthesia, a medical condition known as malignant hyperthermia may occur resulting in death of the patient. The symptoms for such a condition include a sudden rise in body temperature of the patient followed shortly thereafter by death. Where such sudden body temperature rises can be detected in time, clinical procedures can be implemented which would save the life of the patient. Devices of the prior art for measuring body temperature have used temperature sensing devices such as thermisters or thermocouples placed in the rectum, esophagus or tympanic membrane, however, they are difficult to use routinely. Devices for measuring body temperatures in the trachea have not been used in the past because they get in the way of the endotracheal tube used to administer anesthesia and their temperature readings are affected by the incoming air temperature, unless a rebreather system is used, which prevents an accurate, constant reading of body temperature. To continuously monitor body temperature within the trachea, such measurements, in order to provide meaningful information, must either not be affected by any cool incoming air entering the trachea or must have a time constant sufficient to measure the temperature of the air exhaled by the patient in order to relate the air temperature to body temperature.

SUMMARY OF THE INVENTION

To insure meaningful constant body temperature measurement, the apparatus of the present invention includes a pliant flexible tube which is adapted to enter the trachea while still permitting the respiratory function to continue. The tube comprises a wall portion, a central air channel, and interior end adapted to enter the trachea and an exterior end, the interior end including a temperature sensor which is attached to or is integral with the tube wall portion extending to the exterior end of the tube and thence to a temperature measuring or indicating device. An inflatable cuff is provided proximate the interior end of the tube on which the temperature sensor can be attached. Thermal insulation may be provided between the temperature sensor and the air channel to insure consistant readings. Rapid temperature detection can be achieved by using a temperature indicating coating applied to the inside of the tube to measure air temperature or to a thermal conductor in thermal connection with the trachea.

It is, therefore, an object of the present invention to provide a device for measuring body temperature within the trachea.

It is a further object of the present invention to provide a device for measuring body temperature at the tracheal wall while still permitting the respiratory function to continue.

It is another object of the present invention to provide a body temperature measurement device using an inflatable cuff disposed about the interior end of an endotracheal tube.

It is a further object of the present invention to provide a body temperature measuring device for measuring relatively rapid temperature increases in body temperature.

It is still another object of the present invention to provide a body temperature measuring device using a temperature indicating coating for measuring tracheal temperature as indicated by exhaled air.

These and other objects of the present invention will become manifest upon study of the following detailed description when taken together with the drawings.

BRIEF DESCRIPTION OF THE DRAWINGS

FIG. 1 is an elevations view of a cuffed endotracheal tube showing the location of the temperature sensor, the temperature measuring device and the apparatus for inflating the cuff.

FIG. 2 is an elevational view of an uncuffed endotracheal tube showing the location of the temperature sensing device and its associated temperature measuring apparatus.

FIG. 3 is an enlarged elevational cross-sectional view of the interior end of the cuffed endotracheal tube of FIG. 1.

FIG. 4 is an enlarged elevational cross-sectional view of the interior end of the uncuffed endotracheal tube of FIG. 2.

DESCRIPTION OF THE PREFERRED EMBODIMENT

Figure 6:
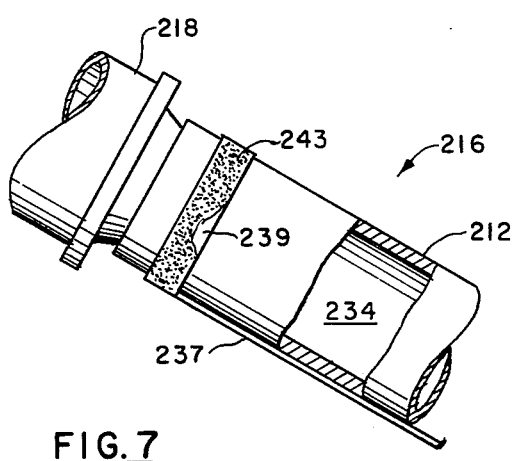
FIG. 6 is a partial elevational sectional view of the exterior end of the cuffed endotracheal tube of FIG. 5.

With reference to FIG. 1 there is illustrated the cuffed endotracheal tube temperature measuring device 10 of the present invention which comprises, basically, a pliant flexible tube 12 having an interior end 14 which is adapted to enter the trachea and an exterior end 16 whch is adapted to connect to clinical respiratory apparatus or anesthesia machine (not shown) through conduit 18.

An inflatable cuff 20 is provided circumferentially about tube 12 proximate interior end 14 and is connected to indicator balloon 22 by means of conduit 24 whch is attached to tube 12 along the major portion of its length.

A conduit 26 is connected to inflation indicator balloon 22, distal conduit 24 and terminates in vent fitting 28 which is provided with stopper 30 to maintain air pressure in cuff 20.

A temperature sensor 36 is located in association with cuff 20, in the present instance, sensor 36 is attached to the interior wall of cuff envelope 38, and is connected by electrical conductors 40a and 40 b to temperature measuring or indicating apparatus 42.

For convenience, a connector plug 44 is provided in conductors 40a and 40b to allow sensor 36 of device 10 of the present invention to be conveniently disconnected from temperature measuring apparatus 42.

Temperature measuring or indicating apparatus 42 can be any apparatus common in the art which is compatible with the type of temperature sensor 36 used. For example, where temperature sensor 36 is a resistance temperature sensor, temperature measuring device 42 would, of course, be a Wheatstone Bridge, a device well known in the art. Where temperature sensor 36 is a thermocouple, for example, a copper-constantan or an iron-constantan thermocouple, temperature measuring device 42 would be a milli-voltmeter. Where temperature sensor 36 is a thermister, temperature measuring device 42 can be any of a number of electronic devices used for measuring low currents and voltages.

In lieu of an electrical temperature sensor 36 (or 136 of FIGS. 2 and 4), a chemical or crystalline temperature detector can be used, such as, a thin coating of a temperature indicating material, common in the art, that changes color upon reaching a predetermined temperature. Such chemical combinations include polymerizable plastics that change color upon polymerization at predetermined temperatures. Other combinations include wax crayon materials that change color at certain predetermined melting temperatures. Such devices are known to be marketed under the trademark "Tempstick." Still other combinations include device that detect changes that move a diaphragm like device to create light wave interference fringes which result from pressure-temperature changes.

Figure 5:
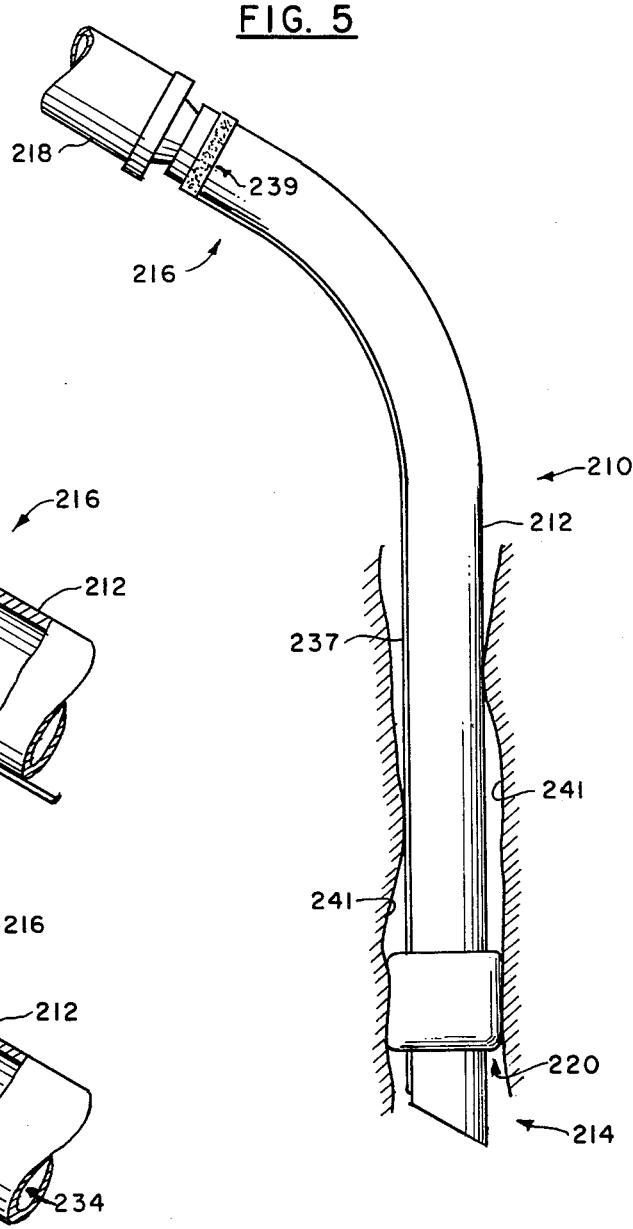
FIG. 5 is an elevational view of another embodiment of the cuffed endotracheal tube temperature measuring device of the present invention utilizing a temperature indicating coating and a thermal conductor.

For example, with reference to FIG. 5 and 6, there is illustrated a cuffed endotracheal tube 210 comprising a tube portion 212 having an interior end 214 adapted to enter the trachea and an exterior end 216, shown inserted in a trachea with cuff 220 inflated to engage tracheal wall 241. The inflation apparatus for cuff 220 is not shown in FIG. 5 since it is similar to the cuff inflation apparatus of FIG. 1.

Along the exterior surface of tube 212 is attached thermal conductor 237, such as copper or silver wire, which extends from interior end 214 to exterior end 216 where it terminates in thermally conductive band 239 which is attached to an encircles tube 212. On the exterior surface of band 239 is a coating of a temperature indicating material or chemical 243, that is, a chemical or material or crystalline combination that changes color upon reaching a temperature indicative of a dangerously high body temperaturem for example, a body temperature of from 101° to 103° F. or higher.

Where tube 212 is fabricated from a transparent plastic, band 239, with its temperature indicating coating viewable through the plastic, may be located along the inside surface of tube 212.

Figure 7:
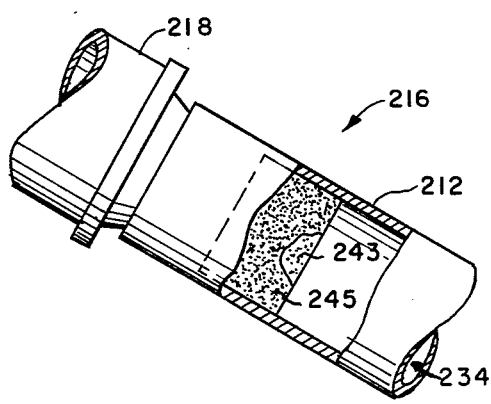
FIG. 7 is a partial elevational sectional view of theexterior end if the cuffed endotracheal tube showing the use of a temperature indicating coating to measure exhaled air temperature.
Figure 8:
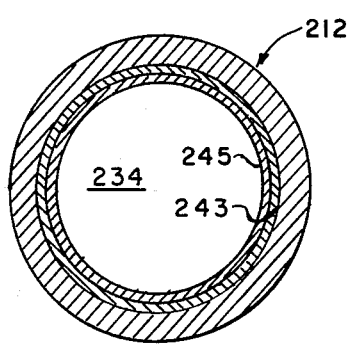
FIG. 8 is a cross-sectional view of the endotracheal tube of FIG. 7 taken at line 8—8.

With reference to FIGS. 7 and 8, there is illustrated an additional embodiment of the medical temperature measuring device of the present invention in which a temperature indicating coating 243 is applied to the inside surface of tube 212 proximate exterior end 216. Tube 212 is, in such a configuration, fabricated from a transparent plastic material, well known in the art, such as polyethylene or the like, to permit color changes to be seen from outside the tube.

A thin protective coating 245 may be used to protect coating 243 from moisture or body fluids. Coating 245 must, of course, be thin to insure rapid response to temperature changes by coating 243.

Since the temperature of the exhaled air from the patient's lungs will bear a relationship to the patient's body temperature, and since coating 243 has a low thermal mass, the temperature of the exhaled air can be detected by the color of the temperature indicating coating 243 when the patient's body temperature and resulting higher exhaled air reaches a predetermined level indicating a dangerous temperature rise, approximately 101° to 103° F. or higher.

With particular reference to FIG. 3, temperature sensor 36 is shown connected to the inside wall of cuff envelope 38 with electrical conductors 40a and 40b passing through conduit 34 which is also used to provide air to inflate and deflate cuff 20. Conduit 24 is also fabricated from a pliant flexible material and is attached to tube 12 or it may be incorporated as a part of tube wall 12. The inside diameter of conduit 24 must, therefore, be sufficiently large to permit both the passage of conductors 40a and 40b as well as the free flow of air through conduit 24 into and out of cuff 20.

Although not shown in FIG. 3, conductors 40a and 40b could be attached to or embedded in the wall of tube 12.

Disposed circumferentially about tube 12 and attached to tube wall 32 is thermal insulation material 35. Typically, insulation material 35 can be fabricated from a number of different materials such as foamed polystyrene or the like. Cuff envelope 38 is attached to the outer surface of periphery of insulation material 35 thus providing a thermal barrier between temperature sensor 36 and air channel 34. In another configuration (not shown) thermal insulation material could be attached to and located within cuff envelope 38 with cuff envelope 38 attached to tube wall 32, in effect, envelope 38 would be sandwiched between tube wall 32 and insulation material 35. In this configuration, thermal insulation material 35 would not be exposed to any body fluids.

Such insulation, in addition to the air contained in cuff envelope 38 and the thermal insulation offered by tube wall 32, will further reduce false temperature readings of sensor 36 due to the variation in the temperature between inhaled and exhaled air flowing in air channel 34 and the temperature of tracheal wall 41.

With reference to FIG. 2, in certain instances such as operations on infants, a cuffed endotracheal tube is not used. In such case, the uncuffed endotracheal tube 110 is used which comprises a tube 112 having an interior end 116 which is adapted to enter the trachea of the infant and an exterior end 116 which is adapted to be connected to a respiratory apparatus or anesthesia machine well known in the art (not shown) through conduit 118.

Temperature sensor 136 is located proximate interior end 114 and is connected by electrical conductors 140a and 140b (FIG. 4) to temperature measuring apparatus 142 which is similar to temperature measuring apparatus 42 of FIG. 1. A connector plug 144 is provided for convenience in connecting uncuffed endotracheal device 110 to temperature measuring or indicating apparatus 142.

With reference to FIG. 4, tube 112 comprises tube wall 132 which encloses air channel 134. Disposed within tube wall 132 at interior end 114 is disposed thermal insulation material 135 which is located between air channel 134 and temperature sensor 136.

As shown, in FIG. 4, temperature sensor 136 is located on the surface of tube wall 132 exterior of air channel 134 and, for its protection, is covered with thermally conductive material 137, such as silver or tantalum or the like, or it can be coated with a thin coating of plastic material such as polyethylene or the like to protect it from body fluids. The thermal mass of the conductive material should be kept small in order to insure a fairly rapid thermal response time.

As shown in FIG. 4, conductors 140a and 140b are incorporated in tube wall 132 in a groove 139 which has been filled with a plastic material similar to the material from which tube 132 is fabricated. Electrical conductors 140a and 140b could also be attached to the exterior of tube 112 provided the conductors are suitably protected by a plastic material to shield them from body fluids found in the trachea and provided such covering does not include any sharp protuberances which might cause injury to the tracheal wall 141. Conductors 140a and 140b could also be located along the interior of tube wall 132 provided the distance between temperature sensor 136 and the point of entrance of conductors 140a and 140b into air channel 134 is sufficiently long to prevent false temperature readings due to thermal conduction along electrical conductors 140a and 140b.

To operate the apparatus of the present invention, cuffed endotracheal tube 10 is prepared for entry into the trachea by removing plug 30 from vent fitting 28 to deflate cuff 20. Tube 10 is then inserted into the trachea as far as necessary for normal clinical procedures. Plug 30 is then placed over vent fitting 28 and a syringe (not shown), well known in the medical art, is placed in is operated in inject air into cuff 20 inflating it to the operating position shown in FIG. 3 with cuff envelope 38 pressing against tracheal wall 41. Temperature measuring device 42 Balloon 22 is used as a pressure indicator for the cuff inflation system. Temperature measuring apparatus 42 is connected to conductors 40a and 40b by plug 44 thus permitting temperature measurement or indicating apparatus 42 to begin measuring tracheal wall 41 temperature. Temperature measuring apparatus 42 can be either a direct reading dial instrument, digital reading device or strip recorder to provide a permanent record of tracheal temperature.

Upon termination of the operation, plug 30 is removed from vent fitting 28 to deflate cuff 20 thus permitting endotracheal tube 10 to be withdrawn from the trachea.

In a similar manner, uncuffed endotracheal apparatus 110 can be operated, however, without the need for the cuff inflation procedure.

Also, in a similar manner, endotracheal tube 210 can be operated with the temperature indication being seen as the change in color of temperature indicating material or coating 243.

Thus, apparatus for measuring tracheal and body temperature is provided.

I claim:

1. A medical temperature measuring device comprising
    means defining a pliant flexible tube adapted to enter the trachea and permit respiratory function to continue, said tube having a tube wall portion, means defining an air channel, an exterior end and an interior end adapted to enter the trachea,
    an inflatable cuff disposed proximate said interior end of said tube and adapted to engage the wall of the trachea when inflated,
    means for inflating said cuff,
    means defining a conduit connected to said tube in fluid communication with said cuff and said means for inflating said cuff,
    a temperature sensor disposed on said cuff and adapted to be in thermal contact with the wall of said trachea when said cuff is inflated,
    means for thermally insulating said temperature sensor from said air channel, said means for thermally insulating said temperature sensor disposed between said sensor and said air channel,
    means for measuring temperature detected by said temperature sensor, and
    means for operatively connecting said temperature sensor to said means for measuring temperature.

2. The apparatus as claimed in claim 1 further comprising
    means for protecting from body fluids said means for thermally insulating said temperature sensor.

* * * * *